United States Patent [19]

Wehrli

[11] Patent Number: 4,821,717
[45] Date of Patent: Apr. 18, 1989

[54] BARBED ELECTROLYSIS AND THERMOLYSIS NEEDLE

[76] Inventor: Janet M. M. Wehrli, 12820 Drexel St., Omaha, Nebr. 68137

[21] Appl. No.: 174,211

[22] Filed: Mar. 28, 1988

[51] Int. Cl.⁴ ............................................. A61B 17/41
[52] U.S. Cl. .............................................. 128/303.18
[58] Field of Search ...................... 128/303.18, 303.13, 128/303.17, 303.19, 355, 642, 784; 433/102

[56] References Cited

U.S. PATENT DOCUMENTS

| | | | |
|---|---|---|---|
| 2,994,324 | 8/1961 | Lemos | 128/355 |
| 3,035,580 | 5/1962 | Guiorguier | 128/303.18 |
| 3,578,745 | 5/1971 | Garnier et al. | 433/102 |
| 3,598,108 | 8/1971 | Jamshidi | 128/2 B |
| 3,651,812 | 3/1972 | Samuels | 128/303.18 |
| 4,074,718 | 2/1978 | Morrison | 128/303.14 |
| 4,216,775 | 8/1980 | Cottingham | 128/303.18 |
| 4,562,838 | 1/1986 | Walker | 128/303.14 |

FOREIGN PATENT DOCUMENTS 7419264  9/1974  Fed. Rep. of Germany ...... 128/642

Primary Examiner—Lee S. Cohen
Attorney, Agent, or Firm—John A. Beehner

[57] ABSTRACT

An electrolysis needle includes a shank having an elongated blade extended therefrom, the blade diameter being between approximately 2 and 10 mils. The blade has a series of barbs formed on it and arranged in axially and circumferentially spaced apart relation. The barbs are inclined outwardly and away from the tip so as to facilitate insertion of the blade into a hair follicle and debriding of the follicle upon removal of the blade.

20 Claims, 3 Drawing Sheets

BARBED ELECTROLYSIS AND THERMOLYSIS NEEDLE

BACKGROUND OF THE INVENTION

The present invention is directed generally to a needle for use in hair removal by electrolysis and thermolysis processes and more particularly to such a needle including a barbed blade.

Electrolysis is a hair removal process that uses direct electrical current to electrochemically destroy the germinative cells of a hair follicle. Electrolysis generally has been known since approximately 1875. In electrolysis, a thin blade having a diameter approximating the diameter of a removed hair is attached to a negative electrode via a shank portion of the needle and inserted into the hair follicle to the base of the follicle where the dermal papilla is located.

Thermolysis, on the other hand, is a hair removal process that uses radio waves or microwaves to generate heat in the follicular tissue to cause destruction through desiccation. In thermolysis, the thin needle is operatively connected to an epilator, having an assigned frequency, for generating the waves transmitted to the needle.

Alternatively, electrolysis and thermolysis can be performed simultaneously with the same needle in a process referred to as the blend.

For sake of brevity and clarity, "electrolysis" shall be hereinafter used generally to refer to electrolysis, thermolysis and/or the blend.

A problem with plain, conventional electrolysis needles is that, whereas the heat is first generated at the tip of the blade in accordance with the "point effect," the heat is rather quickly conducted up the shaft of the blade so as to be felt by the nerve endings adjacent the patient's skin surface, causing pain. Another problem with conventional needles is hair regrowth in approximately 15 to 50% of the follicles operated upon due to ineffective treatment for any of a variety of reasons.

Whereas thin broaches having somewhat barb-like protrusions are used by dentists for root canal operations, the protrusions on such broaches function solely as mechanical cutting or scraping tools, not as heat dissipating extensions of the broach. Such root canal broaches are typically provided with a manual grip which is not designed to be supported in any separate broach holding tool.

Accordingly, a primary object of the present invention is to provide an improved electrolysis needle and method.

Another object is to provide an improved electrolysis needle and method which eliminate most of the discomfort associated with hair epilation techniques.

Another object is to provide an improved electrolysis needle which concentrates heat near the hair papilla and lower two-thirds of the follicle, thus protecting the surface epidermis.

Another object is to provide an electrolysis needle which dissipates heat by providing a low thermal resistance between the blade and the tissue within the hair follicle to allow for greater heat transfer and more uniform heat dissipation.

Another object is to provide an improved electrolysis needle and method which prevent unnecessary damage to the tissue in the upper third of the follicle above the isthmus region.

Another object is to provide an improved electrolysis needle and method which insure a fast healing rate.

Another object is to provide an improved electrolysis needle and method which reduce tissue inflammation.

Another object is to provide an improved electrolysis needle and method which prevent or minimize possible side effects as scarring and blanching of the tissue due to overtreatment.

Another object is to provide an improved electrolysis needle and method which effect a high percentage of total follicle destruction per insertion of the blade into the hair follicle.

Another object is to provide an improved electrolysis needle and method which result in a lesser number of treatments being necessary for complete eradication of the hair-producing cells.

Finally, another object is to provide an improved electrolysis needle which is simple and rugged in construction, economical to manufacture and efficient in operation.

SUMMARY OF THE INVENTION

The electrolysis needle of the present invention is adapted for use in a conventional electrolysis needle holder and includes an elongated blade having a diameter of between 0.002 and 0.010 inches over the substantial portion of the length thereof and an elongated shank secured to the end of the needle opposite the tip. The blade includes a plurality of axially and circumferentially spaced apart barbs protruding from it. The barbs are preferably inclined outwardly and away from the tip so as to facilitate insertion of the blade and yet effect a debriding of the follicle upon removal of the blade. The barbs effect a lower thermal resistance between the blade and surrounding tissue and thereby delay the heat transfer up the needle where it would be felt at the surface of the skin. Accordingly, the barbed blade of the needle of this invention makes electrolysis more comfortable for the patient as well as more effective than with conventional needles.

DESCRIPTION OF THE PREFERRED EMBODIMENT

Figure 1:
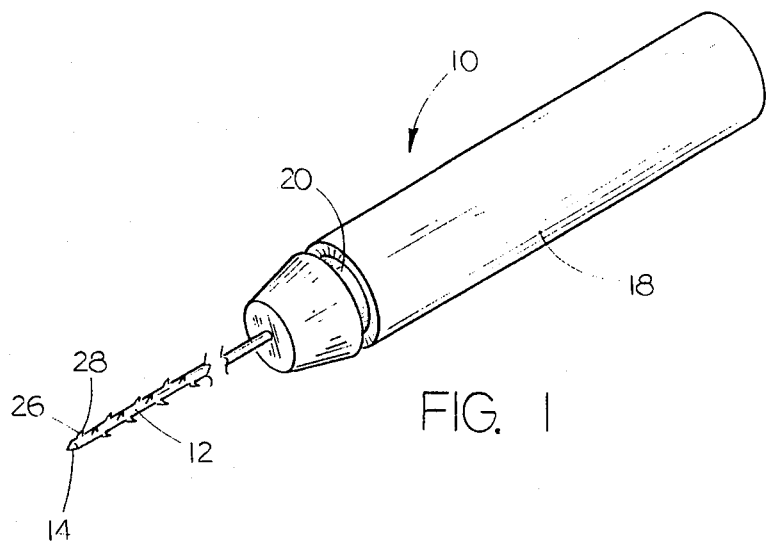
FIG. 1 is a perspective view of the electrolysis needle of the invention.
Figure 2:
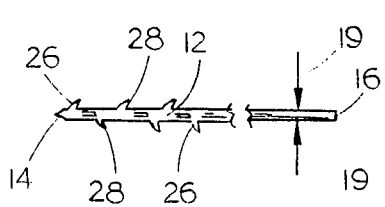
FIG. 2 is a partial and foreshortened enlarged side elevational view of the barbed blade.

The improved electrolysis needle 10 of the present invention is illustrated in FIGS. 1 and 2 as including an elongated barbed blade 12 having a tip 14 and an opposite end portion 16 permanently secured to a substantially wider diameter shank 18.

Figure 3:
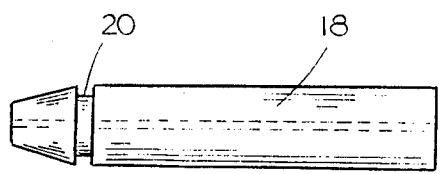
FIG. 3 is a side elevational view of the shank of the electrolysis needle.
Figure 4:
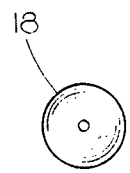
FIG. 4 is an end view of the shank of FIG. 3.
Figure 5:
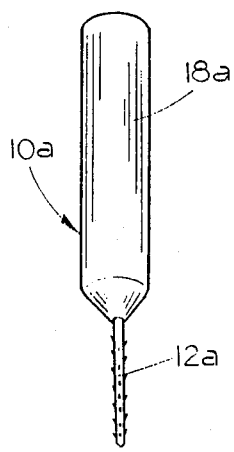
FIG. 5 is a side elevational view of an electrolysis needle including an integrally formed blade and shank.

The shank 18 may be a separate tubular sleeve as shown in FIGS. 1 and 3, within which the opposite end portion 16 of the blade is permanently secured by any suitable means. One common securement means is a mechanical crimp as at 20 in FIGS. 1 and 3, which may be of any type including a swedging crimp, four point crimp and others. Alternatively, the shank 18a may be integrally formed with the blade 12a, as shown in FIG. 5, or a shank may be formed by wrapping a wire of copper or the like around one end of the blade.

The blade 12 may be made of a high quality surgical stainless steel such as AISI 301 or 302 austenitic stainless steel or any other suitable material. The shank 18 is either the same material as the blade, as in an integral needle 10a, or preferably of a high quality surgical stainless steel in a two part needle. The size of the shank 18 is 0.050 inches in outer diameter by one-half inch long. This size has been the standard in the profession for over fifty years.

Figure 6:
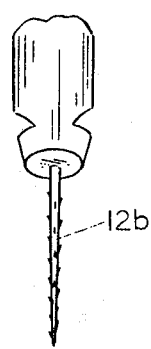
FIG. 6 is a partial perspective view of an electrolysis needle having a tapered blade.
Figure 7:
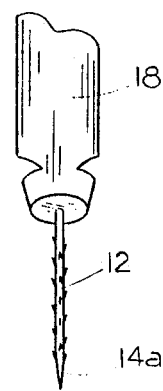
FIG. 7 is a partial perspective view of an electrolysis needle including a straight blade with a tapered tip.
Figure 8:
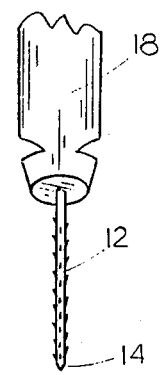
FIG. 8 is a partial perspective view of an electrolysis needle with a straight blade having a conical tip.
Figure 9:
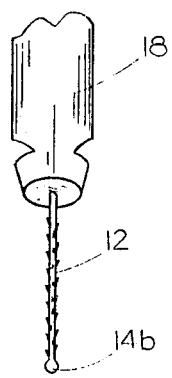
FIG. 9 is a partial perspective view of an electrolysis needle including a straight blade having a bulbous tip.
Figure 10:
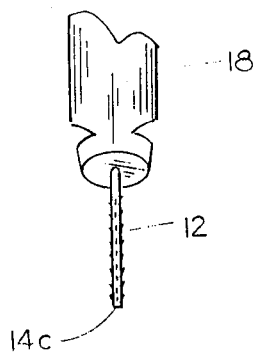
FIG. 10 is a partial perspective view of an electrolysis needle including a straight blade with a blunt tip.
Figure 11:
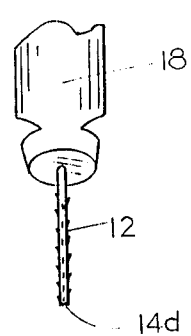
FIG. 11 is a partial perspective view of an electrolysis needle including a straight blade with a jagged end.
Figure 12:
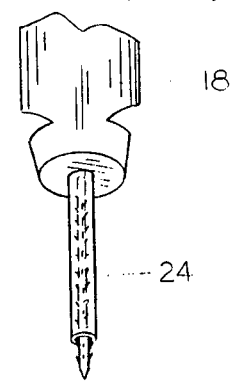
FIG. 12 is a partial perspective view of an electrolysis needle with a straight blade partially covered by insulation material.

Electrolysis blades are available in any number of different shapes, such as the straight blade 12 of FIG. 2 or the blade 12b having the long taper as illustrated in FIG. 6. Any shaped blade may be formed with any of various shaped tips including a tapered tip 14a (FIG. 7), conical tip 14 (FIG. 8), bulbous tip 14b (FIG. 9), blunt cut 14c (FIG. 10) or jagged end 14d (FIG. 11), as illustrated on the straight blades of these figures. For purpose of example, the blade 12 illustrated in FIGS. 1 and 2 is a straight blade having a conical tip 14. Likewise, blades may be formed with different degrees of flexibility and with or without any of various types of insulation coatings 24 thereon, as shown in FIG. 12.

The diameter of a straight blade, the distance between arrows 19 in FIG. 2, is generally within the range between 0.001 and 0.010 inches and preferably between 0.002 and 0.007 inches. The diameter of a tapered blade will decrease toward the tip end with the diameter at any selected position along the blade, generally falling within the above ranges.

The blade 12 may be provided in any of various lengths, with the dimension of the exposed portion being generally within the range between 2 and 15 millimeters and preferably between 2 and 8 millimeters. The following chart sets forth common diameters and lengths of blades corresponding to the designated sizes.

| CHART OF STANDARD NEEDLE SIZES | | | |
|---|---|---|---|
| STRAIGHT BLADE | | | |
| | Blade Diameter | Blade Length | |
| Size | inches | inches | mm |
| 2½ S | .0025 | 5/32 to 6/32 | 4 |
| 3 S | .003 | 5/32 to 6/32 | 4 |
| 3 M | .003 | 7/32 to 8/32 | 6 |
| 3 L | .003 | 9/32 to 10/32 | 8 |
| TAPERED BLADE | | | |
| | Blade Diameter | | Blade Length |
| Size | Tip | Widest Part** | inches | mm |
| 2.4 S | .002 | .004 | 5/32 to 6/32 | 4 |
| 3.4 S | .003 | .004 | 5/32 to 6/32 | 4 |
| 3.4 M | .003 | .004 | 7/32 to 8/32 | 6 |
| 3:4 L | .003 | .004 | 9/32 to 10/32 | 8 |

**The widest part of the blade which can be inserted into the follicle.

Not all manufacturers adhere closely to these designated sizes, so not all needles labeled "number 3" are actually 0.003 inches in diameter —they may be 0.0035 inches or even 0.004 inches in diameter, for example.

Figure 13:
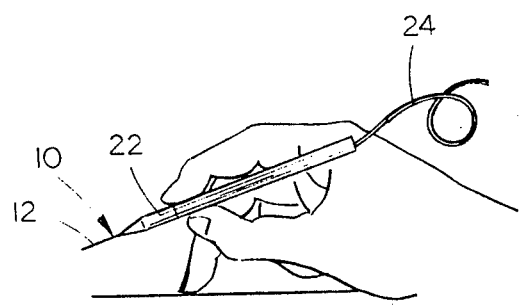
FIG. 13 is a diagrammatic illustration of the electrolysis needle inserted within a hand-held electrolysis needle holder.
Figure 14:
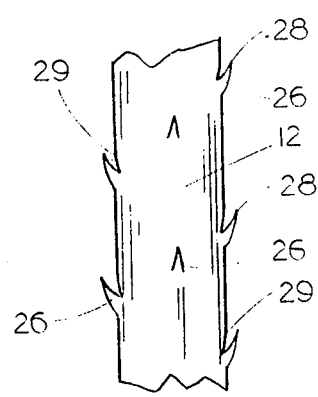
FIG. 14 is an enlarged partial side view of a straight needle showing the needle surface gouged to form the barbs.
Figure 15:
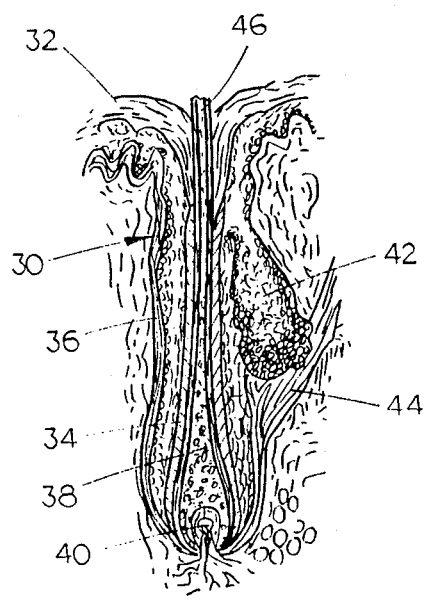
FIG. 15 is a diagrammatic side sectional view of a hair follicle.

The shank 18 of needle 10 is adapted for insertion into the conventional electrolysis needle holder 22, as illustrated in FIG. 13. p The improvement of the invention is directed to the provision of a plurality of barbs 26 arranged in axially and circumferentially spaced relation along the length of the blade 12, as illustrated in FIGS. 1 and 2. Whereas the barbs are preferably of substantially uniform size and shape and have their tips 28 inclined rearwardly away from the blade tip 14 as shown. The term "barb" is used herein generally to describe a projection from the surface of the blade. The barbs 26 may be formed by a gouging or machining process whereby the surface 29 of the blade is gouged to displace material for forming the barb 26 as shown in FIG. 14. The radial dimension from the tip of a barb to the surface 29 of the blade is generally between 0.0001 and 0.004 inches and preferably between 0.0005 and 0.003 inches.

A preferred arrangement for the barbs is a plurality of substantially axial rows with the barbs being axially spaced apart by a dimension of between 0.01 and 0.10 inches and preferably between 0.01 and 0.06. Between three and eight such rows of barbs would be sufficient with four rows being preferred for manufacturing efficiency.

Figure 16:
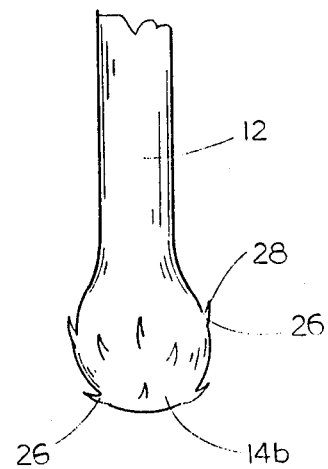
FIG. 16 is an enlarged partial side view of the tip end of a straight blade having a bulbous tip including a plurality of barbs thereon.

Another alternative is to confine the barbs to the tip of the blade, as illustrated in FIG. 16 in connection with a bulbous tip, for example. A further alternative is to provide barbs on both the tip and along the surface of the blade.

A description of the operation of the improved electrolysis needle of the invention requires reference to a hair follicle 30, as illustrated in FIG. 6. A follicle 30 is a pouch-like depression in the skin or epidermis 32 and includes an outer root sheath 34 which is enclosed within a connective tissue sheath 36. The outer root sheath will remain through all the hair-growth cycles. To the contrary, an inner root sheath 38 grows along with a hair and is removed when a hair is extracted. A dermal papilla 40 is situated at the base of the follicle.

About two-thirds up the hair follicle a sebaceous gland 42 is formed as an expanded portion of the external root sheath to discharge sebum fluid onto the adjacent surface of the skin to act as a lubricant and possibly nutrient. An arrector pili muscle 44 is situated just below the sebaceous gland for limited movement of the hair in response to temperature changes and the like. The hair itself is indicated at 46.

In operation, electrolysis is performed with the needle of the invention as follows. First, the needle 10 is inserted into the needle holder 22 of an epilation machine, the frequency of which is approved by the FCC. With the needle holder held in the manner illustrated in FIG. 13, for example, the blade 12 is then inserted into the hair follicle to the extent of engagement of the blade tip 14 with the base or dermal papilla 40 of the follicle 30. The point of engagement can be easily felt by an experienced operator.

Figure 17:
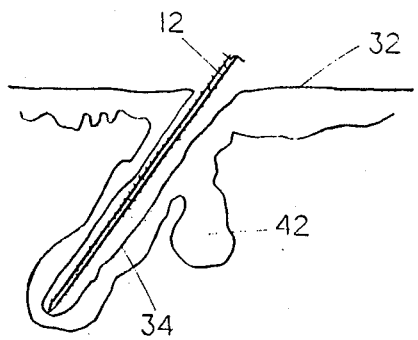
FIG. 17 is a diagrammatic side sectional view of a hair follicle with the barbed needle inserted therein.
Figure 18:
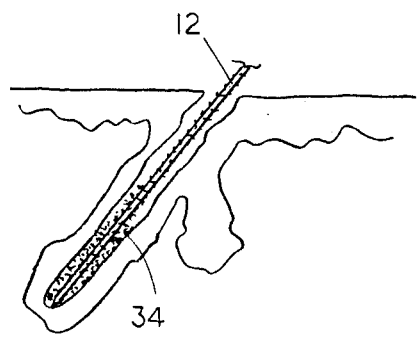
FIG. 18 is a diagrammatic side sectional view of a hair follicle with dots indicating the application of heat within the hair follicle.
Figure 19:
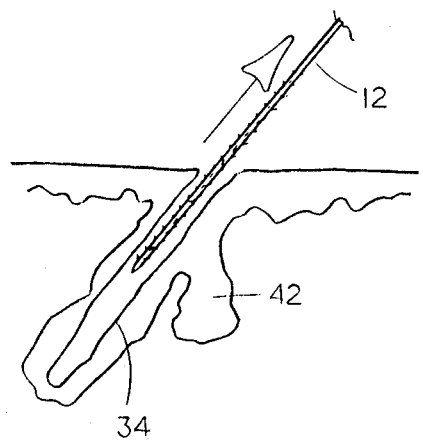
FIG. 19 is a diagrammatic side sectional view illustrating the barbed blade being withdrawn from the hair follicle.

The angle at which the blade is inserted depends on the angle at which the hair is growing. For example, a hair that grows straight up requires the blade to be inserted straight. If a hair is growing at an angle, as indicated in FIGS. 17–19, the blade will be inserted at that same angle. It is preferred that the blade not engage the surface of the skin 32 when treating hairs that grow at an angle close to the skin since that contact can result in unnecessary pain and scabbing.

Once the blade is inserted, a measured amount of energy, i.e., either electrical current or radio waves, is transmitted through the needle to the follicle. The amount of energy used depends on various factors relative to the type and dimensions of the hair follicle itself, as well known by those experienced in electrolysis. Conditions and techniques for varying the intensity/time ratio are well known to those skilled in the art of electrolysis. Experience has shown that the epilation settings currently used for other needles should generally be reduced for use with the improved needle of the present invention. The provision of barbs on the blade portion of the needle 10 provides a low thermal resistance between the needle itself and the tissue within the hair follicle 30 which allows for a greater heat transfer and more uniform heat dissipation. It is theorized that the improved dispersement of heat by the barbed blade of the invention may accommodate higher settings than those used by conventional blades, while nevertheless avoiding pain to the patient.

The dots indicated in FIG. 18 indicate the pattern of heat within the hair follicle. The heat is concentrated in the lower third of the follicle where the regenerative portions of the follicle are effectively destroyed and where heat is not sensed by the nerve endings in the epidermis close to the surface of the skin. Due to the "point effect," heat originates at the tip of the needle and progresses upwardly in time. The improved heat transfer by the barbs, which act somewhat like cooling fins of an air cooled internal combustion engine, significantly delays the transfer of heat axially up the shaft of the needle.

Finally, the needle 10 is lifted to withdraw the blade 12 from the follicle 30 as indicated in FIG. 19. Upon withdrawal, the barbs effect a debriding of the hair follicle by physically scraping and removing tissue therefrom. This debriding effect, when combined with heat treatment of electrolysis, improves the overall efficiency of the needle for effectively preventing regrowth. This may be accounted for by the destruction of the follicular epithelium which plays a crucial role in hair regrowth. Early signs of follicular cell injury suggest eventual destruction of these cells and hence permanent depilation because it has been shown that lysosomal proteolytic enzymes are present in follicular epithelium and become active immediately following injury. Such activity is particularly detrimental to prekeratinous proteins such as hair. Use of the barbed needle of the invention requires a new technique. Suggested settings for obtaining the best "working point", in order of preference, are as follows:

---
1. Intensity -- Low
   Time -- Adjusted to working point.
2. Time -- Low
   Intensity -- Adjusted to working point.
---

To avoid increasing time and intensity, one of the following procedures may be used: (1) double insertion of the blade into each follicle, or (2) on a single insertion technique, use a "tap-pause-tap" series with the foot pedals of the epilation machine.

Another preferred technique is to move the fully inserted blade up and down within the follicle in a plunger action to scape destroyed tissue from the wall of the follicle and move it upwardly out of the way. The vertical reciprocating movement of the blade effects an improved direct heat transfer between the blade and follicle wall as compared to heat transfer through the necrotized tissue.

If the improved barbed needle of the invention is not disposed of after use, it may be cleaned by rubbing it on the soaped bristles of a toothbrush, for example, rinsed and resterilized before each use.

Whereas the invention has been shown and described in connection with preferred embodiments thereof, it is understood that many modifications, substitutions and additions may be made which are within the intended broad scope of the appended claims.

Thus there has been shown and described an improved barbed electrolysis needle which accomplishes at least all of the stated objects.

I claim:

1. An electrolysis needle, adapted for use in an electrolysis needle holder, said needle comprising,
   an elongated blade having a tip at one end and an opposite end,
   said blade having a diameter of between 0.002 and 0.010 inches over a substantial portion of the length thereof,
   an elongated electrolysis shank aligned with said blade and secured to the opposite end thereof, said shank having a diameter substantially greater than said blade for insertion within an electrolysis needle holder, and
   said blade including a plurality of axially and circumferentially spaced apart barbs protruding therefrom.

2. The electrolysis needle of claim 1 wherein said barbs are inclined radially outwardly and axially away from the tip of the blade.

3. The electrolysis needle of claim 2 wherein the radial extent of said barbs from said blade is between 0.001 and 0.005 inches.

4. The electrolysis needle of claim 2 wherein said barbs have pointed free ends.

5. The electrolysis needle of claim 1 wherein said blade is tapered from said opposite end toward the tip.

6. The electrolysis needle of claim 1 wherein said blade is of substantially uniform diameter along the length thereof.

7. The electrolysis needle of claim 1 wherein said barbs are arranged in generally axially extended rows with the barbs in each row spaced apart by a distance of between 0.02 and 0.06 inches.

8. The electrolysis needle of claim 7 wherein said blade includes between three and five axial rows of barbs.

9. The electrolysis needle of claim 1 wherein said barbs are arranged on the exposed surface of the blade excluding the tip.

10. The electrolysis needle of claim 1 wherein said barbs are arranged on the tip of the blade.

11. The electrolysis needle of claim 10 wherein additional barbs are arranged on the exposed surface of the blade between the tip and shank.

12. The electrolysis needle of claim 1 wherein said blade and shank are integrally formed as a single solid needle.

13. The electrolysis needle of claim 1 wherein said shank comprises a sleeve having the opposite end of said blade received therein.

14. The electrolysis needle of claim 13 wherein said shank includes a radial crimp to secure said blade within said shank.

15. A method of permanently removing hair by electrolysis, comprising providing an electrolysis needle including an elongated blade extending from one end of an electrolysis shank, said blade having a tip at one end a plurality of axially and circumferentially spaced apart barbs protruding therefrom, inserting the electrolysis shank into an electrolysis needle holder, manipulating the needle holder to insert the barbed blade into a hair follicle, causing energy to be transmitted through the needle holder and needle to the follicle thereby destroying tissue of the follicle, withdrawing the barbed blade from the follicle and thereby debriding the follicle by scraping and removing destroyed tissue on the barbs of the blade.

16. The method of claim 15 wherein said manipulating step comprises inserting the barbed blade into a hair follicle to the extent of engagement with the dermal papilla of the follicle.

17. The method of claim 16 wherein said step of causing energy to be transmitted includes reducing the epilation settings from those used with unbarbed blades.

18. The method of claim 17 wherein said step of causing energy to be transmitted includes using a "tap-pause-tap" operation of the foot pedals of an epilation machine.

19. The method of claim 16 further comprising reinserting the blade into each follicle, causing energy to be transmitted through the reinserted blade and withdrawing the reinserted blade from the follicle.

20. The method of claim 15 further comprising vertically reciprocating said barbed blade within the hair follicle before withdrawing the barbed blade from the follicle.

* * * * *